United States Patent [19]

Stahl

[11] Patent Number: 5,071,421
[45] Date of Patent: Dec. 10, 1991

[54] METHOD FOR PREVENTING DAMAGE TO TISSUE DURING ULTRASONIC SURGERY

[76] Inventor: Norman O. Stahl, 3199 Montery Dr., Merrick, N.Y. 11566

[21] Appl. No.: 476,982

[22] Filed: Feb. 8, 1990

[51] Int. Cl.$^5$ .............................................. A61F 9/00
[52] U.S. Cl. .................................. 606/107; 606/169
[58] Field of Search .............. 604/22; 606/107, 169; 128/20, 858, 888

[56] References Cited

U.S. PATENT DOCUMENTS

| | | | |
|---|---|---|---|
| 3,528,425 | 9/1970 | Banko | 606/169 |
| 3,618,594 | 11/1971 | Banko | 606/169 |
| 3,857,387 | 12/1974 | Shock | 606/169 |
| 4,033,349 | 7/1977 | Baehr | 606/107 |
| 4,417,578 | 11/1983 | Banko . | |
| 4,515,583 | 5/1985 | Sorich | 606/169 |
| 4,516,398 | 5/1985 | Wuchinich | 604/22 |
| 4,643,185 | 2/1987 | Gaba . | |
| 4,765,329 | 8/1988 | Cumming et al. . | |
| 4,784,138 | 11/1988 | Sinnett . | |
| 4,869,715 | 9/1989 | Sherburne | 604/22 |

*Primary Examiner*—Stephen C. Pellegrino
*Assistant Examiner*—Ralph A. Lewis
*Attorney, Agent, or Firm*—Hoffmann & Baron

[57] ABSTRACT

A method is provided for preventing damage to tissue during microsurgery. The method involves the use of a heat sink in the form of a cylindrical shield which is inserted within an incision prior to the use of an ultrasonic cutting tool. The heat generated by the cutting tool is absorbed by the shield rather than the surrounding tissue, thereby minimizing or eliminating damage to the tissue adjacent the cutting tool. The incision through which the cutting tool extends during an operation accordingly tends to remain in its original state rather than widening due to the effects of heat damage.

7 Claims, 1 Drawing Sheet

5,071,421

METHOD FOR PREVENTING DAMAGE TO TISSUE DURING ULTRASONIC SURGERY

BACKGROUND OF THE INVENTION

The field of the invention relates to microsurgery, and particularly to microsurgery which involves the making of an incision and the use of heat-generating equipment which is inserted through the incision.

Microsurgical systems are used for performing many operations today, including ophthalmic surgery. Systems for removing cataracts, for example, typically include a cutting probe and associated aspiration device for removing macerated tissue to a collection vessel. An irrigation supply is also provided to replace the fluid removed through aspiration.

Devices for performing ocular microsurgery through the use of an ultrasonic generator and vibrating tool have seen widespread use. One such device is described in U.S. Pat. No. 3,589,363. The patented device includes a hand piece including an ultrasonic vibrating tool. Such a tool is used to break up unwanted tissue, such as cataractous tissue, which is then removed via irrigation and aspiration procedures. The tool is inserted through a small incision made in the eye to gain access to the defective lens tissue. The tool extends through the incision during the entire operation as the surgeon breaks up the tissue with the tool and causes its removal. Upon completion of the operation, an artificial lens is implanted in place of the cataractous lens, and the incision is stitched closed. The above procedure is generally known as phacoemulsification.

A number of different types of ultrasonic cutting tools are known to the art. U.S. Pat. Nos. 4,417,578, 4,643,717 and 4,681,561 disclose three such tools. Such tools operate at frequencies above twenty thousand Hz.

The advantage of cataract removal via phacoemulsification is the relatively small wound (incision) necessary to gain access to the cataract. The ultrasonic instrument used to emulsify the cataract generates heat, however, which causes the collagen around the wound to shrink. This tends to open the wound rather than allowing it to remain as a slit. If the wound is closed tightly, the cornea will be distorted, causing astigmatism. If the wound is not closed tightly, it will tend to leak. In addition, the iris may not stay in place if the wound is not tightly closed.

There is accordingly a need for a method which allows full advantage to be taken of the small incisions made in surgical procedures such as phacoemulsification.

SUMMARY OF THE INVENTION

An object of the invention is to provide a method for minimizing or eliminating the damage caused by a heat-generating surgical instrument to an incision through which the instrument extends.

It is another object of the invention to provide a method for performing ocular ultrasonic surgery which allows an incision to be closed tightly without causing significant side effects such as astigmatism.

In accordance with these and other objects of the invention, a method is provided which includes the steps of: making an incision through body tissue, inserting a shield within the incision such that the shield defines a passage through the incision, inserting an ultrasonic tool through the passage defined by the shield, and actuating the ultrasonic tool.

The shield is preferably capable of absorbing heat which would ordinarily be absorbed by the tissue surrounding the wound. It is also preferably flexible so that it can conform to the shape of the incision without damaging tissue.

DETAILED DESCRIPTION OF THE INVENTION

The invention relates to a microsurgical procedure which minimizes the effects of heat generated in the area of an incision by an operating tool. It will be described with respect to cataract surgery, although the procedure would be applicable to any microsurgical technique which involves making an incision which may later be subjected to the damaging effects of heat.

Cataract surgery involves the removal of cataractous lens tissue from the eye. The removed tissue may subsequently be replaced by an artificial (plastic) lens.

There are several known methods of removing cataractous tissue. One currently popular method is the phacoemulsification procedure. This procedure is preferred by many surgeons as it requires an incision which is only several millimeters in length. Once the incision is made, an ultrasonic cutting tool is directed to the cataractous lens tissue. The tool generally includes a sleeve and axial bore for carrying fluid to the site of the operation and removing fluid and tissue therefrom. The site is accordingly subjected to combined irrigation and aspiration as the vibrating cutting tool breaks up the tissue mass. Because this procedure takes at least several minutes, the tissue surrounding the cutting tool is ordinarily subjected to the heat generated by the ultrasonically vibrated tool.

Figure 1:
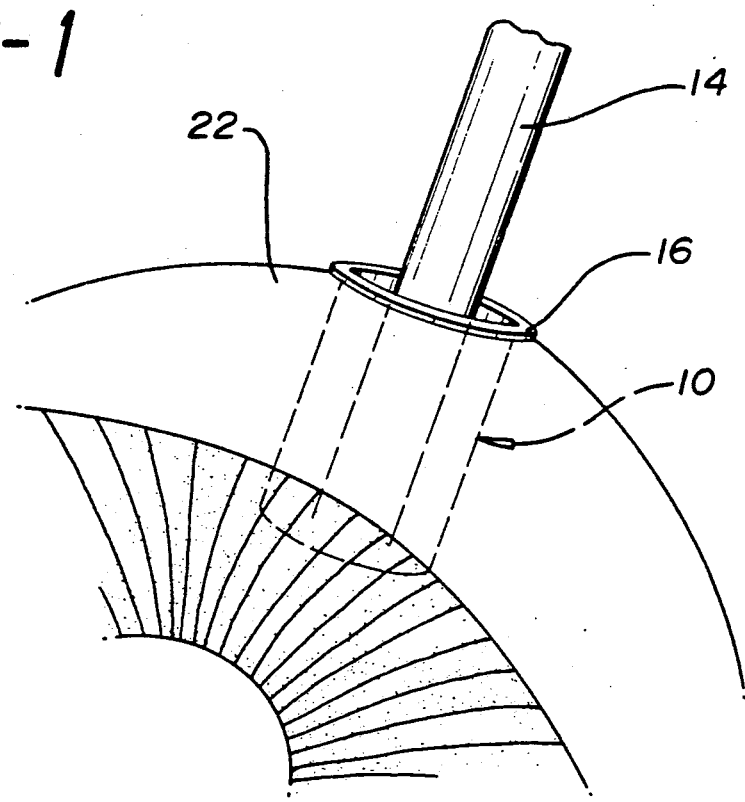
FIG. 1 is an enlarged perspective view of an eye surgery procedure wherein an ultrasonic cutting tool is employed.

In order to avoid collagen shrinkage or other problems associated with the heat generated by an ultrasonic cutting tool, a sleeve or shield 10 is inserted within the incision as shown in FIG. 1. The shield 10 is preferably made from a flexible material, such as Teflon, which can absorb the heat which would otherwise be absorbed by the tissue surrounding the incision. The length of the shield should be at least approximately equal to the thickness of the cornea where it is to be used as part of a phacoemulsification procedure. It is preferably longer so that a portion of the shield extends outside the body for easy removal once the operation has been completed.

The shield 10 defines a walled passage 12 through which the cutting tool 14 is inserted. Both the inner and outer surfaces of the shield are smooth in order to facilitate its insertion within the incision and to allow the cutting tool to be moved axially without dislodging the shield. The shield can either be inserted independently into the incision or simultaneously with the cutting tool. The flexibility of the shield allows it to be squeezed from its natural cylindrical configuration to an elliptical or flat shape where it more easily fits within the incision, as shown in FIG. 1.

Figure 3:
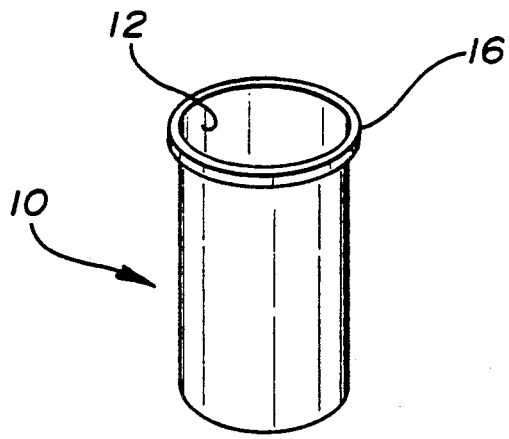
FIG. 3 is an enlarged perspective view of a second type of shield adapted for insertion within an incision.
Figure 4:
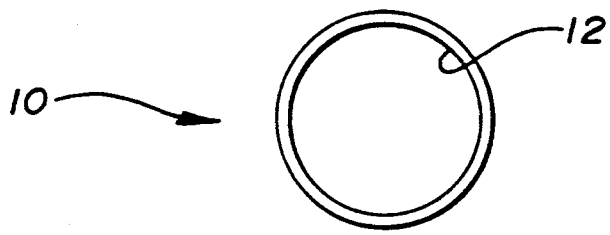
FIG. 4 is a top plan view thereof.

The shield 10 may be formed as a tube, as shown in FIGS. 1, 3 and 4. A flanged end 16 is preferably formed at one end of the tube to prevent the shield from inadvertently being pushed too far into the incision. The opposite end of the tube is straight to facilitate insertion and withdrawal thereof.

Figure 2:
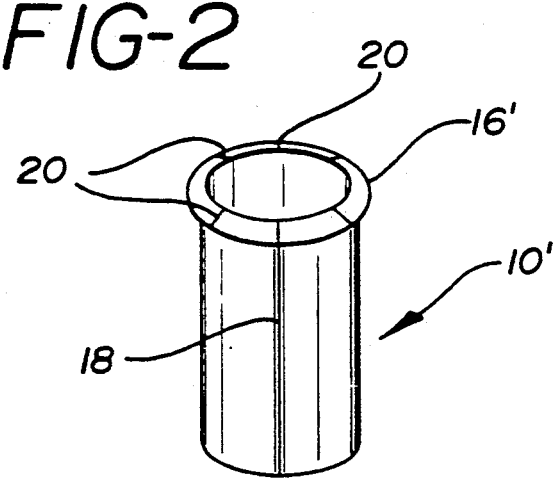
FIG. 2 is an enlarged perspective view of a shield adapted for insertion within an incision.

Alternatively, a shield 10' may be constructed from a flat, substantially rectangular piece of material and folded into the cylindrical configuration shown in FIG. 2. The edges of the shield would overlap each other, as shown at 18. The top of the flat piece of material, and therefore the tube formed therefrom, may include slits 20 to allow the top portion thereof to be folded over as shown in FIG. 2. The flanged end 16' formed by this procedure functions in the same manner as that described with respect to the flange 16 of the previously described shield 10 having an endless wall. In use, the manufacturer or the surgeon simply rolls up the flat piece of material into the tubular form shown in FIG. 2, and then inserts it within the incision. The overlapping portions of the shield may or may not be sealed prior to use.

Upon completion of the phacoemulsification procedure, the cutting tool 14 is withdrawn. The flanged end of the shield 10 or 10' is grasped, and the shield squeezed to better conform to the slit-like configuration of the incision. An artificial lens may be inserted through the incision at this point. The incision is stitched closed either following withdrawal of the cutting tool 14 or insertion of the artificial lens. Various methods of lens insertion are described in U.S. Pat. Nos. 4,530,117, 4,643,185, 4,765,329 and 4,781,719, disclosures of which are incorporated by reference herein.

By virtue of employing a shield as discussed herein during the period of operation of the ultrasonic cutting tool, the incision remains generally in the form of a slit as the surrounding collagen is generally undamaged. The stitching procedure accordingly does not cause the eye tissue 22 to be stretched in the manner which would otherwise occur if collagen shrinkage due to excessive heat had taken place. Such shrinkage tends to open a wound, thereby requiring the surgeon to pull the opposing ends thereof a greater distance in order to close it than if the wound had remained as a slit. As discussed above, such pulling of eye tissue will generally result in astigmatism if the incision is closed to the desired extent. Astigmatism is reduced or avoided through the practice of the invention.

It will be appreciated that the shield may be made from various materials provided they are sufficiently inert to avoid reaction with the patient. While preferably flexible, the shield may be partially or entirely rigid in construction. It should also be able to absorb a sufficient amount of the heat generated adjacent thereto. The shield may be cylindrical, elliptical or any other configuration which would allow its placement within the incision and the passage of the shaft of a cutting tool therethrough.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A microsurgical process comprising the steps of:
   making an incision through body tissue;
   providing a flexible shield having a generally cylindrical configuration;
   squeezing said shield into a flattened configuration;
   inserting the flattened shield within the incision such that the flattened shield defines a passage through the incision;
   inserting an ultrasonic cutting tool through the passage defined by the shield;
   actuating the ultrasonic cutting tool,
   whereby the shield protects the body tissue surrounding the incision from heat generated by the ultrasonic cutting tool.

2. A process as described in claim 1 including the steps of withdrawing the ultrasonic cutting tool from the passage, squeezing the shield, and withdrawing the shield from the incision.

3. A process as described in claim 1 wherein the shield includes a flanged end, including the step of inserting the shield within the incision such that the flanged end thereof remains outside of the incision.

4. A process as described in claim 1 wherein said body tissue is eye tissue, including the steps of contacting the lens of the eye with an end of the ultrasonic cutting tool, breaking up the lens by ultrasonically vibrating the cutting tool, removing the lens, withdrawing the ultrasonic cutting tool, removing the shield from the incision, and stitching the incision to a substantially closed position.

5. A process as described in claim 1 wherein the shield is formed as a cylinder having an endless wall.

6. A microsurgical process comprising the steps of:
   making an incision through body tissue;
   providing a flat, substantially rectangular piece of flexible material;
   folding said piece of flexible material into a shield having a naturally cylindrical configuration;
   inserting said shield within the incision, said shield defining a passage through the incision;
   inserting an ultrasonic cutting tool through the passage defined by the shield; and
   actuating the ultrasonic cutting tool;
   whereby the shield protects the body tissue surrounding the incision from heat generated by the ultrasonic cutting tool.

7. A microsurgical process comprising the steps of:
   making an incision through body tissue;
   providing a shield having a naturally cylindrical configuration and an open end including a plurality of slits, said slitted end being folded outwardly;
   inserting said shield within the incision such that said slitted end remains outside the incision, the shield defining a passage through the incision;
   inserting an ultrasonic cutting tool through the passage defined by the shield; and
   actuating the ultrasonic cutting tool,
   whereby the shield protects the body tissue surrounding the incision from heat generated by the ultrasonic cutting tool.

* * * * *